US012765752B2

(12) United States Patent
Bluemler et al.

(10) Patent No.: US 12,765,752 B2
(45) Date of Patent: Oct. 20, 2026

(54) DEVICE FOR MOVING A MAGNETIC OBJECT IN A CONTAINER

(71) Applicant: Sekels GmbH, Ober-Moerlen (DE)

(72) Inventors: Peter Bluemler, Ingelheim am Rhein (DE); Dietrich Sekels, Rockenberg (DE); Stefan Hiebel, Friedberg (DE)

(73) Assignee: Sekels GmbH, Ober-Moerlen (DE)

( * ) Notice: Subject to any disclaimer, the term of this patent is extended or adjusted under 35 U.S.C. 154(b) by 317 days.

(21) Appl. No.: 18/686,918

(22) PCT Filed: Sep. 16, 2022

(86) PCT No.: PCT/DE2022/100691

§ 371 (c)(1),
(2) Date: Feb. 27, 2024

(87) PCT Pub. No.: WO2023/057007

PCT Pub. Date: Apr. 13, 2023

(65) Prior Publication Data

US 2024/0349991 A1 Oct. 24, 2024

(30) Foreign Application Priority Data

Oct. 5, 2021 (DE) ..................... 10 2021 125 870.7

(51) Int. Cl.
*A61B 1/00* (2006.01)

(52) U.S. Cl.
CPC ................................ *A61B 1/00158* (2013.01)

(58) Field of Classification Search
None
See application file for complete search history.

(56) References Cited

U.S. PATENT DOCUMENTS

| | | | | |
|---|---|---|---|---|
| 6,535,092 | B1 | 3/2003 | Hurley et al. | |
| 2003/0015474 | A1* | 1/2003 | Sterman .................. | B03C 1/035 210/695 |
| 2006/0232369 | A1* | 10/2006 | Gorshkov ............ | G01R 33/383 335/306 |
| 2011/0140458 | A1* | 6/2011 | Arnold ................... | H02K 35/04 290/1 R |
| 2011/0301452 | A1 | 12/2011 | Maschke et al. | |

FOREIGN PATENT DOCUMENTS

| | | | |
|---|---|---|---|
| DE | 10 2010 022 926 | A1 | 12/2011 |
| DE | 10 2016 014 192 | A1 | 5/2018 |
| EP | 2 347 699 | B1 | 11/2018 |

OTHER PUBLICATIONS

Machine translation of DE 102016014192 A1 (Year: 2018).*
Machine translation of EP 2347699 A1 (Year: 2011).*
(Continued)

*Primary Examiner* — Bernard Rojas
(74) *Attorney, Agent, or Firm* — Collard & Roe, P.C.

(57) ABSTRACT

A device for moving a magnetic object in a container has two pairs of dipoles grouped around the container. Between the pairs of dipoles a pair of mutually concentrically surrounding quadrupoles is arranged. The dipoles and the quadrupoles are in the form of a Halbach cylinder. In this way, the magnetic object can be moved through the container particularly efficiently.

8 Claims, 4 Drawing Sheets

(56) References Cited

OTHER PUBLICATIONS

Figure 1:
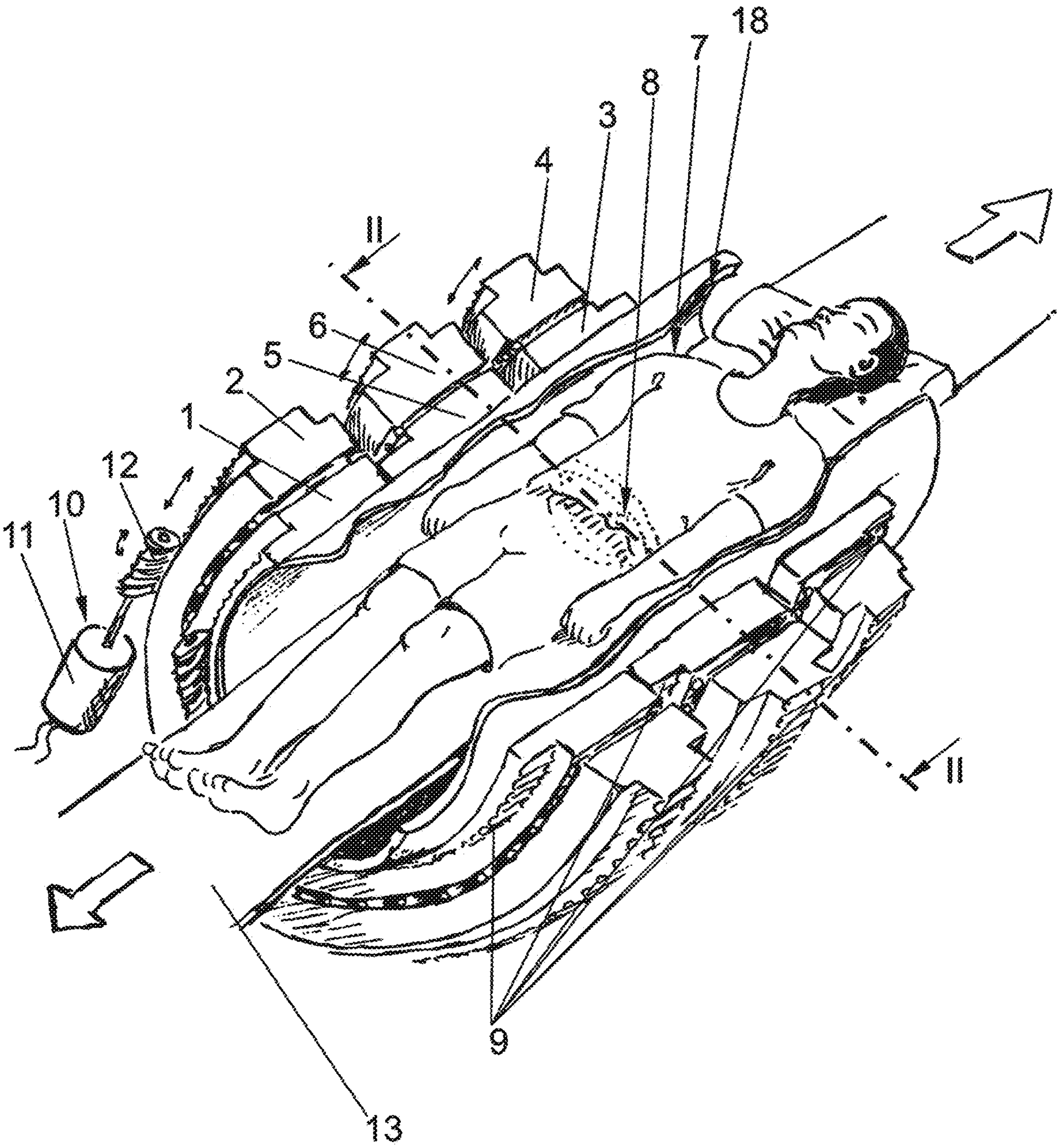

A. C. Bakenecker et al, "A concept for a magnetic particle imaging scanner with Halbach arrays", Sep. 29, 2020, Phys. Med. Biol. vol. 65, No. 19, p. 195014, XP020357577, DOI: 10.1088/1361-6560/AB7E7E, ISSN:0031-9155, total of 15 pages.
Oleg Tretiak et al, "Variable single-axis magnetic-field generator using permanent magnets", arxiv.org, Cornell University Library, 201 Olin Library Cornell University Ithaca, NY 14853, Nov. 9, 2018, XP081048213, total of 7 pages.
T. O'Reilly et al, "Three-dimensional MRI in a homogenous 27 cm diameter bore Halbach array magnet", Aug. 20, 2019, Journal of Magnetic Resonance vol. 307, XP085839542, DOI: 10.1016/J.JMR.2019.106578, ISSN:1090-7807, total of 9 pages.
International Search Report in PCT/DE2022/100691, mailed Jan. 2, 2023.

* cited by examiner

DEVICE FOR MOVING A MAGNETIC OBJECT IN A CONTAINER

CROSS REFERENCE TO RELATED APPLICATIONS

This application is the National Stage of PCT/DE2022/100691 filed on Sep. 16, 2022, which claims priority under 35 U.S.C. § 119 of German Application No. 10 2021 125 870.7 filed on Oct. 5, 2021, the disclosure of which is incorporated by reference. The international application under PCT article 21(2) was not published in English.

The invention relates to a device for moving a magnetic object in a container, having dipoles grouped around the container and a quadrupole, wherein the magnetic fields of the dipoles and of the quadrupole can be moved relative to one another.

Such a device is known, for example, from DE 10 2016 014 192 A1. With this device, it is possible to displace the object within a space. This is done by means of a magnetic force that can be adjusted in terms of intensity and direction.

From DE 10 2010 022 926 A1, a method for positioning a magnetic nano-object at a target location, by means of a magnetic gradient field, has become known. Using this method, an instrument, such as, for example, for thermal ablation or a biopsy needle, can be moved in a human body.

From U.S. Pat. No. 6,535,092 A, it is known to arrange individual magnets in a ring, so as to rotate, and thereby to represent dipoles and quadrupoles in a structure. However, common generation of fields using dipoles and quadrupoles is not provided. With this device, it is therefore possible to introduce only low forces into the object.

The invention is based on the problem of further developing a device of the type stated initially in such a manner that it allows particularly efficient movement of the object in the container.

This problem is solved, according to the invention, in that two pairs of dipoles are arranged in different planes, at a distance from one another, and that two quadrupoles are arranged in a plane between the planes of the two dipoles.

By means of this embodiment, particularly great forces can be introduced into the object, and these forces can be controlled by means of a suitable orientation of the dipoles and the quadrupoles. If, for example, the quadrupoles are brought into a compensation position relative to one another, the object can be held in a center position by the dipoles. The generation of the magnetic fields and of the forces that act on the object is explained in detail in DE 20 2016 014 192 A1, so that reference is made to this document with regard to the disclosure. The object can be objects of different sizes, preferably paramagnetic or supermagnetic objects, and they can contain iron oxides, for example. In accordance with the field of use, the object can have diameters in the millimeter range down to the nanometer or micrometer range.

The arrangement of the dipoles and of the quadrupoles in different planes can be structured in a particularly simple manner, in terms of design, according to another advantageous further development of the invention, if magnets are arranged in Halbach cylinders in order to generate the dipoles and the quadrupoles, and enclose a space intended for the container. In this way, the dipoles and quadrupoles that are arranged in different planes preferably for cylinders arranged axially one behind the other.

An amplification or attenuation of the magnetic field can be achieved in a simple manner, according to another advantageous further development of the invention, if two Halbach cylinders, each having magnets for generating the dipoles and/or the quadrupoles, are arranged concentric to one another.

The intensity of the magnetic fields can be adjusted in a simple manner, according to another advantageous further development of the invention, if the Halbach cylinders, which enclose one another concentrically, can be moved relative to one another.

The dipoles and the quadrupole can be driven around the space in a simple manner, according to another advantageous further development of the invention, if the dipoles and quadrupoles, which are configured as Halbach cylinders, have a drive apparatus, in each instance, and are mounted so as to rotate relative to one another. By means of the drive of the dipoles and the quadrupoles, magnetic fields that result in planned directions can be generated, and thereby the magnetic object can be driven.

A three-dimensional movement of the object can be structured in a particularly simple manner, according to another advantageous further development, if a carriage for holding the container that contains the object can be moved relative to the dipoles and the quadrupoles, and if a relative movement direction of the carriage, relative to the dipoles and the quadrupoles, is arranged parallel to the axis of rotation of the Halbach cylinders.

The object driven by the dipoles and the quadrupoles can be held in the center of the magnetic fields, in a simple manner, according to another advantageous further development of the invention, if the carriage can be displaced parallel to the axis of rotation of the Halbach cylinders. By means of this embodiment, the change in position of the object in the magnetic fields that are generated can be balanced out, so that the object always remains in the center of the device.

The device can be used, in an advantageous manner, to examine a human body or animal body, if the magnetic object is arranged in a probe that is configured to be introduced into the human body or animal body. In this regard, the probe can be configured as an endoscopic capsule or can also have a medical instrument for treatment of the body.

Signals from the interior of the body can be detected in a simple manner, according to another advantageous further development of the invention, if the probe has at least one sensor for capturing data. By means of a suitable arrangement of antennas or memory components, the signals can be optionally stored in memory or transmitted to a reception apparatus situated outside of the body.

The probe can be supplied with electric current using an electric line or a battery, for example. Electric current for supplying the probe can be generated, in a simple manner, according to another advantageous further development of the invention, by means of magnetic induction, if an induction coil is arranged in the probe. By means of this embodiment, no battery or electric line is required.

The device has a particularly simple design, according to another advantageous further development of the invention, if the magnetic object is configured as a permanent magnet. Preferably, the magnetic object is configured in spherical shape.

The invention permits numerous forms of embodiments. For further clarification of its basic principle, one of them is shown in the drawing and will be described hereinafter. The drawing shows, in FIG. 1 a device for moving a magnetic object in a container, FIG. 2 a sectional representation through the device, with the container in the region of the object, along the line II-II from FIG. 1, FIG. 3 in magnification, the object from FIG. 1 in a probe, FIG. 4 schematically, a longitudinal section through an arrangement of dipoles and quadrupoles of the device from FIG. 1, in a first orientation, FIG. 5 the arrangement of dipoles and quadrupoles from FIG. 4 in a different orientation, FIG. 6 a schematic representation of the geometry of Halbach cylinders.

FIG. 1 shows a device having two pairs of diploes 1-4 that enclose one another concentrically, and a pair of quadrupoles 5, 6 that enclose one another concentrically, arranged between the pairs of dipoles 1-4. The dipoles 1-4 and the quadrupoles 5, 6 enclose a space 18, in which a container 7, shown as an example as a human patient, is situated. A magnetic object 8 is situated in the plane of the quadrupoles 5, 6, within the container 7. The dipoles 1-4 and the quadrupoles 5, 6 are each configured as Halbach cylinders, having a length provided for generating magnetic fields in the container 7 to be examined, and each have gear teeth 9 for a drive apparatus 10, in each instance, of which one is shown as an example. By means of the drive apparatuses, the dipoles 1-4 and the quadrupoles can be rotated around the container. The drive apparatus 10 that is shown has an electric motor 11 having a worm-gear drive 12. In alternative embodiments, not shown, the electric motor 11 can stand in engagement with the gear teeth 9 by way of a toothed belt or a gear-wheel transmission. The container 7 lies on a carriage 13. The carriage 13 can be moved by a drive, not shown, parallel to the axis of the Halbach cylinders of the dipoles 1-4 and of the quadrupoles 5, 6, so that the object 8 always lies essentially in the center of the Halbach cylinders of the quadrupoles 5, 6. In the center, the greatest force can be transferred to the object 8 by the dipoles 1-4 and the quadrupoles 5, 6.

Figure 2:
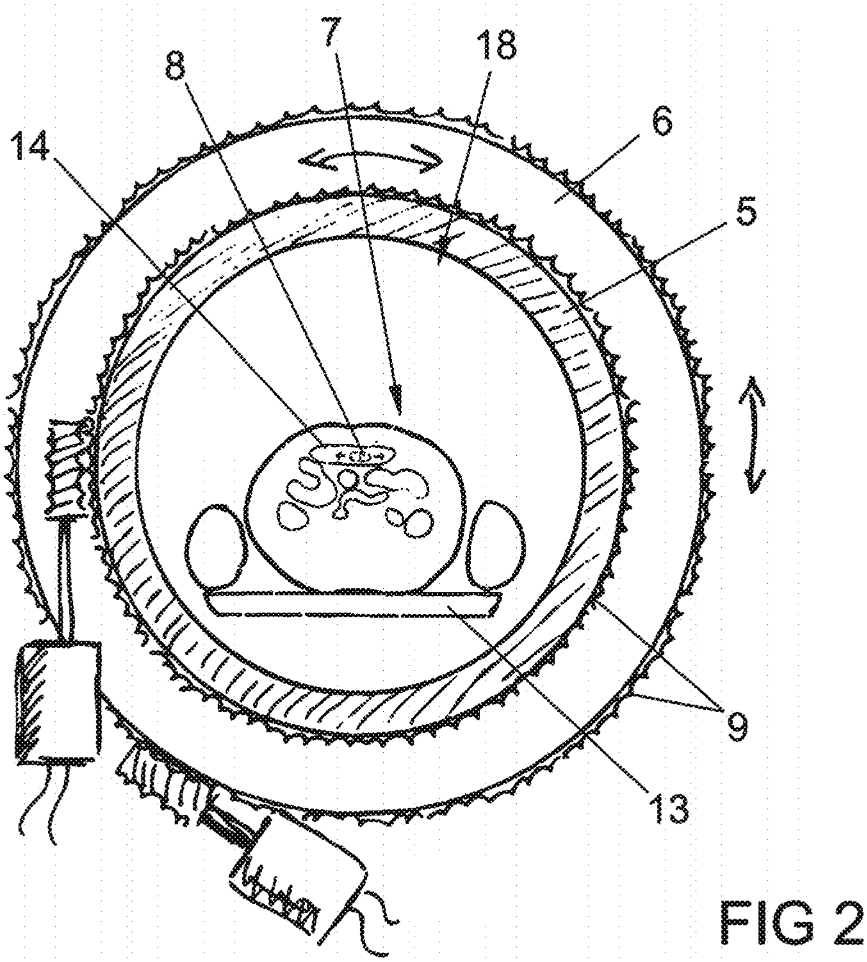

FIG. 2 shows a sectional representation through the device having the container 7 from FIG. 1, along the line II-II. The movements of the carriage 13 and of the dipoles 1-4 and of the quadrupoles 5, 6 are indicated with arrows in FIGS. 1 and 2. For example, the magnetic object 8 is arranged in an endoscopic probe 14 and is moved through the container 7 using the magnetic fields of the dipoles 1-4 and of the quadrupoles 5, 6, as well as the movement of the carriage 13.

Figure 3:
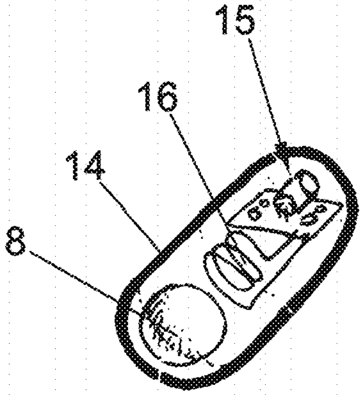
Figure 4:
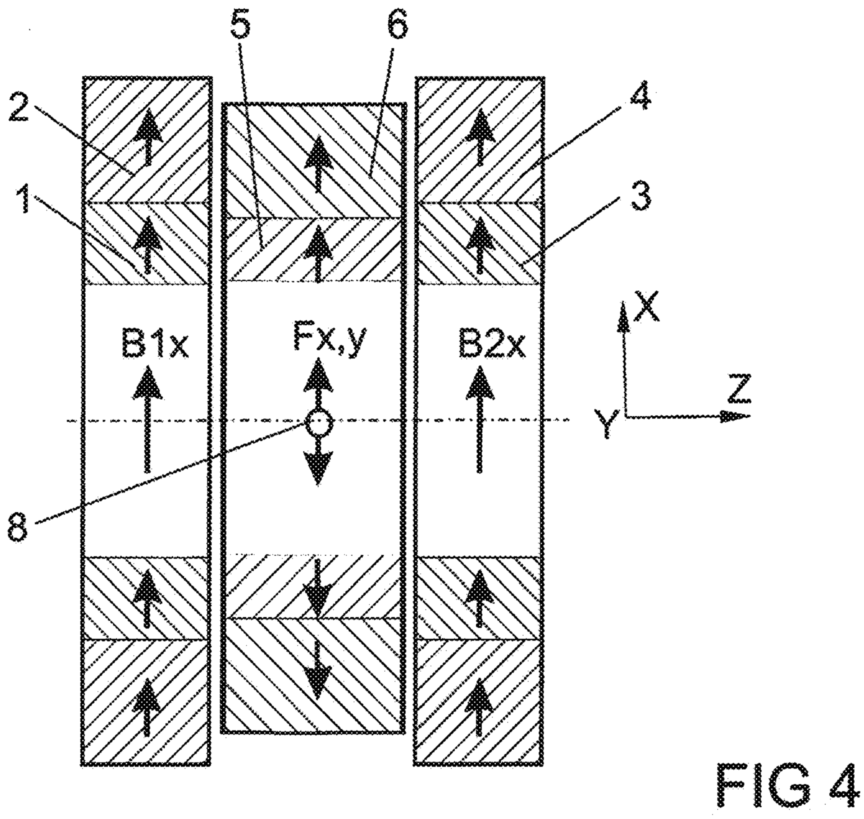

FIG. 3 shows, on a larger scale, the object 8 from FIGS. 1 and 2 arranged in the probe 14. The object 8 is a preferably spherical permanent magnet or magnetizable material. The probe 14 furthermore contains a sensor 15 and an induction coil 16. In an embodiment that is not shown, the probe 14 can furthermore contain a medical tool, for example for a biopsy, for thermal treatment, or the like.

FIG. 4 schematically shows a longitudinal section through the arrangement of the dipoles 1-4 and of the quadrupoles 5, 6 shown in FIG. 1. Arrows shown in the dipoles 1-4 and the quadrupoles 5, 6 represent the magnetic orientation there. The arrows shown in the center and marked with F represent the resulting magnetic force vectors in the planes x, y, and z. The arrows marked with B represent the magnetic flux density. In the orientation shown, the magnetic object 8 is oriented in the x direction, and moved and accelerated in the central xy plane by means of rotation of the two quadrupoles 5, 6.

Figure 5:
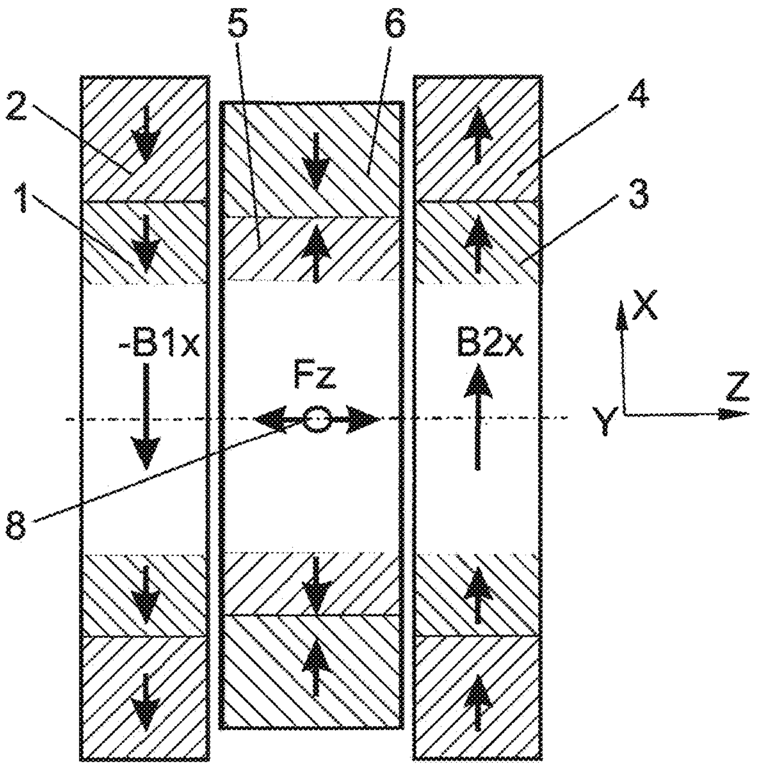

FIG. 5 schematically shows a different orientation, as compared to FIG. 4, of the dipoles 1-4 and the quadrupoles 5, 6 shown in FIG. 1. By means of a corresponding rotation, the two quadrupoles 5, 6 have been brought into a compensation position relative to one another, so that no movement of the object 8 in the xy plane takes place. The dipoles 1-4 have been rotated into an opposite orientation. In this way, a magnetic field gradient is generated along the z direction, and thereby the object 8 is moved in this direction.

Figure 6:
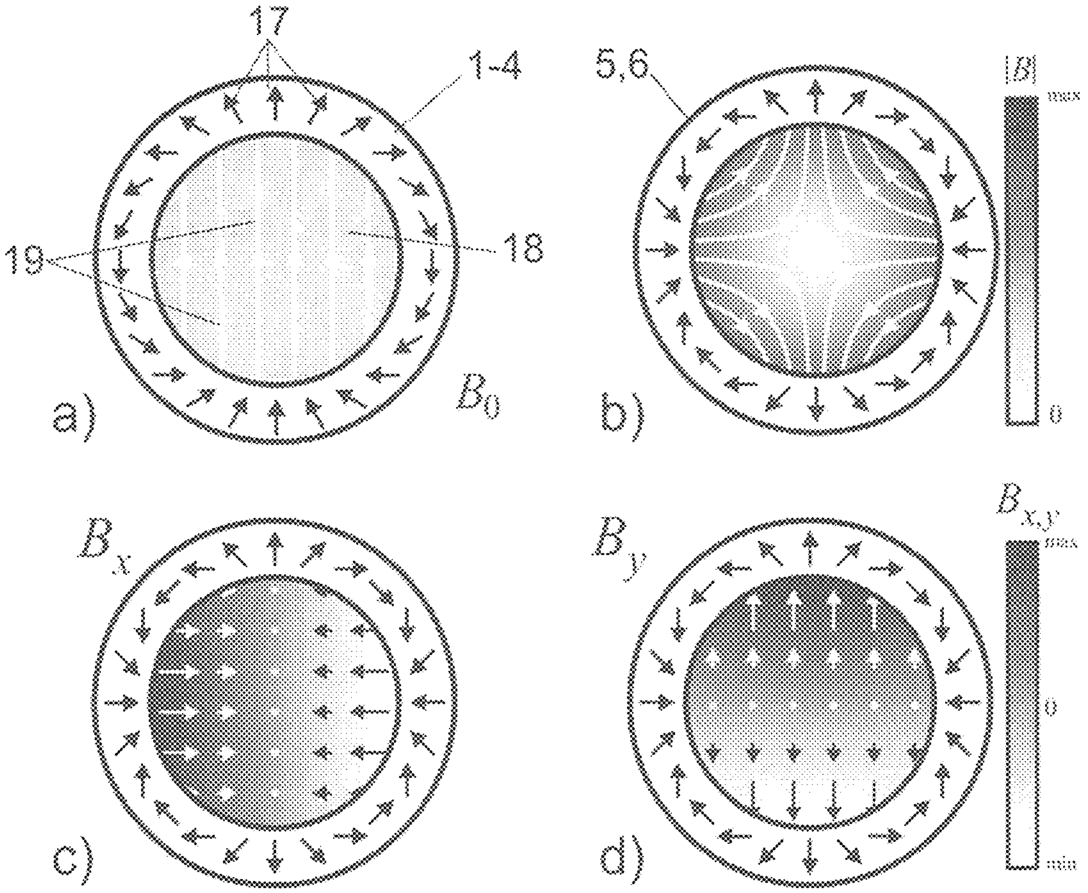

FIG. 6 shows, for clarification, a schematic representation of the geometry of Halbach cylinders: a) shows the dipoles 1-4 described in FIGS. 1 to 5: The homogeneous magnetic field is generated by means of a ring-shaped cylinder composed of permanent magnet material. In this regard, the arrows 17 shown in the cylinder of the dipole 1 indicate the magnetization of this material, which changes continuously over the entire circumference. However, the arrows 17 can also be formed by individual magnets. The amount (intensity) of the magnetic field is represented by means of shading of a space 18 that surrounds the cylinder. The container 7 with the object 8, shown in FIGS. 1 to 5, is arranged in the space 18. Here, the field is homogeneous. The direction of the magnetic field is additionally represented by flow lines 19 marked with arrows. b) shows the quadrupoles 5, 6 shown in FIGS. 1 to 5 in the same representation as a). c) and d) now show the Bx and By component of the magnetic field in b). The black and white arrows now show the intensity and direction of the magnetic field, however (no flow lines). The different intensity of the magnetic field is shown with the shading in a/b and c/d.

The further technological background of the dipoles 1-4 and of the quadrupoles 5, 6 as well as the field gradients produced with them is described in detail in DE 10 2016 014 192 A1, so that reference is made to this document with regard to the disclosure.

The invention claimed is:

1. A device for moving a magnetic object in a container, having dipoles grouped around the container and a quadrupole, wherein the magnetic fields of the dipoles and of the quadrupole can be moved relative to one another, wherein two pairs of dipoles are arranged in different planes, at a distance from one another, and wherein two quadrupoles are arranged in a plane between the planes of the two dipoles, wherein magnets are arranged in Halbach cylinders in order to generate the dipoles and the quadrupoles, and enclose a space intended for the container, wherein the Halbach cylinders, which enclose one another concentrically, can be moved relative to one another, wherein a carriage for holding the container that contains the object can be moved relative to the dipoles and the quadrupoles, and wherein a relative movement direction of the carriage, relative to the dipoles and the quadrupoles, is arranged parallel to the axis of rotation of the Halbach cylinders.

2. The device according to claim 1, wherein two Halbach cylinders, each having magnets for generating the dipoles and/or the quadrupoles, are arranged concentric to one another.

3. The device according to claim 1, wherein the dipoles and quadrupoles, which are configured as Halbach cylinders, have a drive apparatus, in each instance, and are mounted so as to rotate relative to one another.

4. The device according to claim 1, wherein the carriage can be displaced parallel to the axis of rotation of the Halbach cylinders.

5. The device according to claim 1, wherein the magnetic object is arranged in a probe that is configured to be introduced into a human body or an animal body.

6. The device according to claim 3, wherein the probe has at least one sensor for capturing data.

7. The device according to claim 5, wherein an induction coil is arranged in the probe.

8. The device according to claim 1, wherein the magnetic object is configured as a permanent magnet.

* * * * *